(12) United States Patent
Chard et al.

(10) Patent No.: US 7,596,422 B2
(45) Date of Patent: Sep. 29, 2009

(54) DETERMINING ONE OR MORE PROFILE PARAMETERS OF A STRUCTURE USING OPTICAL METROLOGY AND A CORRELATION BETWEEN PROFILE MODELS AND KEY PROFILE SHAPE VARIABLES

(75) Inventors: Jeffrey Alexander Chard, Sunnyvale, CA (US); Junwei Bao, Palo Alto, CA (US)

(73) Assignee: Tokyo Electron Limited, Tokyo (JP)

( * ) Notice: Subject to any disclaimer, the term of this patent is extended or adjusted under 35 U.S.C. 154(b) by 300 days.

(21) Appl. No.: 11/653,062

(22) Filed: Jan. 12, 2007

(65) Prior Publication Data

US 2008/0170242 A1    Jul. 17, 2008

(51) Int. Cl.
*G06F 19/00* (2006.01)
*G01B 9/00* (2006.01)
*G01J 4/00* (2006.01)
*G01N 21/55* (2006.01)
*G01J 3/00* (2006.01)

(52) U.S. Cl. .................. 700/121; 700/108; 700/98; 356/369; 356/300; 356/124; 356/445

(58) Field of Classification Search .............. 700/121, 700/108; 356/369, 300, 124, 445
See application file for complete search history.

(56) References Cited

U.S. PATENT DOCUMENTS

| | | | | |
|---|---|---|---|---|
| 5,889,593 A * | 3/1999 | Bareket | ............... | 356/445 |
| 6,104,486 A * | 8/2000 | Arimoto | ............... | 356/300 |
| 6,483,580 B1 * | 11/2002 | Xu et al. | ............... | 356/300 |
| 6,590,656 B2 * | 7/2003 | Xu et al. | ............... | 356/369 |
| 6,597,463 B1 * | 7/2003 | Singh et al. | ............... | 356/630 |
| 6,657,736 B1 * | 12/2003 | Finarov et al. | ............... | 356/625 |
| 6,891,626 B2 | 5/2005 | Niu et al. | | |
| 6,943,900 B2 | 9/2005 | Niu et al. | | |
| 7,119,893 B2 * | 10/2006 | Littau et al. | ............... | 356/124 |
| 7,388,677 B2 * | 6/2008 | Vuong et al. | ............... | 356/601 |
| 2004/0109173 A1 * | 6/2004 | Finarov et al. | ............... | 356/625 |
| 2004/0267397 A1 | 12/2004 | Doddi et al. | | |
| 2005/0209816 A1 | 9/2005 | Vuong et al. | | |
| 2008/0170241 A1 * | 7/2008 | Chard et al. | ............... | 356/625 |

* cited by examiner

*Primary Examiner*—Ramesh B Patel
*Assistant Examiner*—Sunray R Chang
(74) *Attorney, Agent, or Firm*—Manuel B. Madriaga

(57) ABSTRACT

One or more profile parameters of a structure fabricated on a wafer in a wafer application are determined by developing a correlation between a set of profile models and one or more key profile shape variables. The wafer application has one or more process steps and one or more process parameters. Each profile model is defined using a set of profile parameters to characterize the shape of the structure. Different sets of profile parameters define the profile models in the set. The one or more key profile shape variables include one or more profile parameters or one or more process parameters. A value of at least one key profile shape variable of the process step of the wafer application to be used in fabricating the structure is determined. One profile model is selected from the set of profile models based on the determined correlation and the value of the at least one determined key profile shape variable. The structure is fabricated using the process step and the value of the at least one determined key profile shape variable determined. A measured diffraction signal off the fabricated structure is obtained. One or more profile parameters of the fabricated structure are determined based on the measured diffraction signal and the selected profile model.

23 Claims, 13 Drawing Sheets

DETERMINING ONE OR MORE PROFILE PARAMETERS OF A STRUCTURE USING OPTICAL METROLOGY AND A CORRELATION BETWEEN PROFILE MODELS AND KEY PROFILE SHAPE VARIABLES

BACKGROUND

1. Field

The present application generally relates to optical metrology of a structure formed on a semiconductor wafer, and, more particularly, to determining one or more profile parameters of a structure using optical metrology and a correlation between profile models and key profile shape variables.

2. Related Art

In semiconductor manufacturing, periodic gratings are typically used for quality assurance. For example, one typical use of periodic gratings includes fabricating a periodic grating in proximity to the operating structure of a semiconductor chip. The periodic grating is then illuminated with an electromagnetic radiation. The electromagnetic radiation that deflects off of the periodic grating are collected as a diffraction signal. The diffraction signal is then analyzed to determine whether the periodic grating, and by extension whether the operating structure of the semiconductor chip, has been fabricated according to specifications.

In one conventional system, the diffraction signal collected from illuminating the periodic grating (the measured diffraction signal) is compared to a library of simulated diffraction signals. Each simulated diffraction signal in the library is associated with a hypothetical profile. When a match is made between the measured diffraction signal and one of the simulated diffraction signals in the library, the hypothetical profile associated with the simulated diffraction signal is presumed to represent the actual profile of the periodic grating.

The hypothetical profiles, which are used to generate the simulated diffraction signals, are generated based on a profile model that characterizes the structure to be examined. Thus, in order to accurately determine the profile of the structure using optical metrology, a profile model that accurately characterizes the structure should be used.

SUMMARY

In one exemplary embodiment, one or more profile parameters of a structure fabricated on a wafer in a wafer application are determined by developing a correlation between a set of profile models and one or more key profile shape variables. The wafer application has one or more process steps and one or more process parameters. Each profile model is defined using a set of profile parameters to characterize the shape of the structure. Different sets of profile parameters define the profile models in the set. The one or more key profile shape variables include one or more profile parameters or one or more process parameters. A value of at least one key profile shape variable of the process step of the wafer application to be used in fabricating the structure is determined. One profile model is selected from the set of profile models based on the determined correlation and the value of the at least one determined key profile shape variable. The structure is fabricated using the process step and the value of the at least one determined key profile shape variable determined. A measured diffraction signal off the fabricated structure is obtained. One or more profile parameters of the fabricated structure are determined based on the measured diffraction signal and the selected profile model.

DETAILED DESCRIPTION OF EXEMPLARY EMBODIMENT(S)

In order to facilitate the description of the present invention, a semiconductor wafer may be utilized to illustrate an application of the concept. The methods and processes equally apply to other work pieces that have repeating structures. Furthermore, in this application, the term structure when it is not qualified refers to a patterned structure.

Figure 1A:
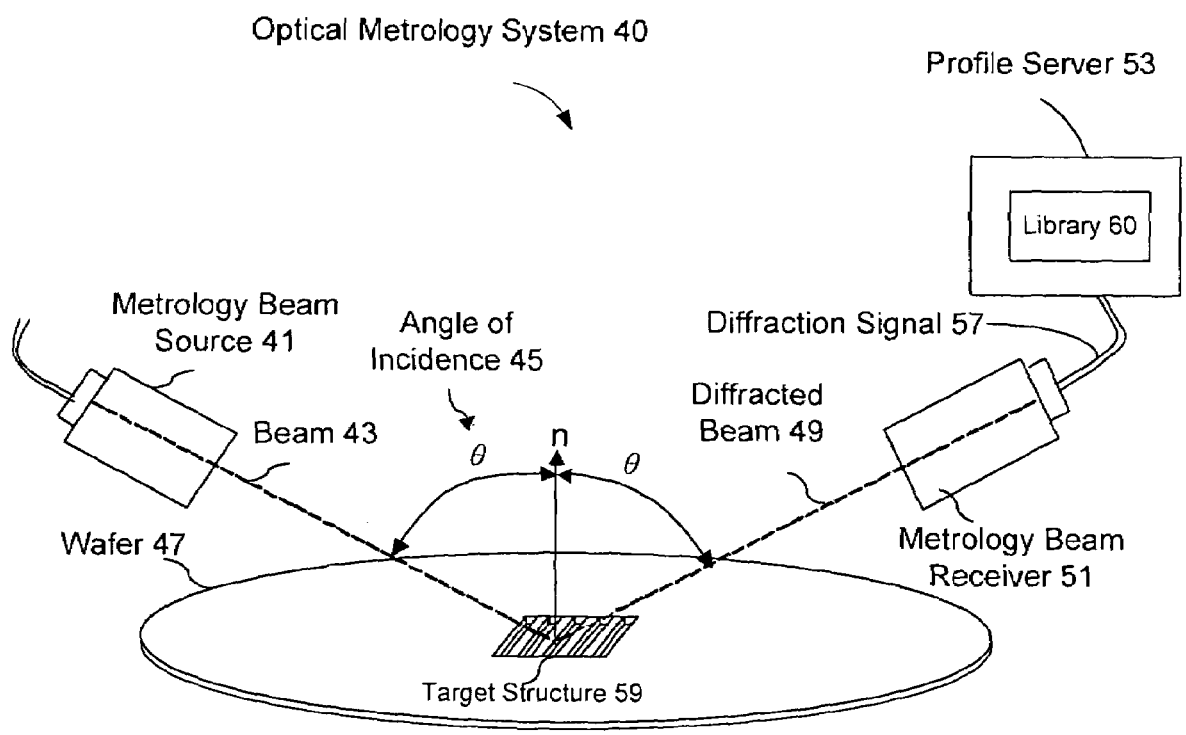
FIG. 1A is an architectural diagram illustrating an exemplary embodiment where optical metrology can be utilized to determine the profiles of structures formed on a semiconductor wafer.

FIG. 1A is an architectural diagram illustrating an exemplary embodiment where optical metrology can be utilized to determine the profiles or shapes of structures fabricated on a semiconductor wafer. The optical metrology system 40 includes a metrology beam source 41 projecting a metrology beam 43 at the target structure 59 of a wafer 47. The metrology beam 43 is projected at an incidence angle θ towards the target structure 59. The diffracted beam 49 is measured by a metrology beam receiver 51. A measured diffraction signal 57 is transmitted to a profile server 53. The profile server 53 compares the measured diffraction signal 57 against a library 60 of simulated diffraction signals and associated hypothetical profiles representing varying combinations of critical dimensions of the target structure and resolution. In one exemplary embodiment, the library 60 instance best matching the measured diffraction signal 57 is selected. The hypothetical profile and associated critical dimensions of the selected library 60 instance are assumed to correspond to the actual cross-sectional shape and critical dimensions of the features of the target structure 59. The optical metrology system 40 may utilize a reflectometer, an ellipsometer, or other optical metrology device to measure the diffraction beam or signal. An optical metrology system is described in U.S. Pat. No. 6,913,900, entitled GENERATION OF A LIBRARY OF PERIODIC GRATING DIFFRACTION SIGNAL, issued on Sep. 13, 2005, which is incorporated herein by reference in its entirety.

Simulated diffraction signals can be generated by applying Maxwell's equations and using a numerical analysis technique to solve Maxwell's equations. It should be noted that various numerical analysis techniques, including variations of rigorous coupled wave analysis (RCWA), can be used. For a more detail description of RCWA, see U.S. Pat. No. 6,891,626, titled CACHING OF INTRA-LAYER CALCULATIONS FOR RAPID RIGOROUS COUPLED-WAVE ANALYSES, filed on Jan. 25, 2001, issued May 10, 2005, which is incorporated herein by reference in its entirety.

Simulated diffraction signals can also be generated using a machine learning system (MLS). Prior to generating the simulated diffraction signals, the MLS is trained using known input and output data. In one exemplary embodiment, simulated diffraction signals can be generated using an MLS employing a machine learning algorithm, such as back-propagation, radial basis function, support vector, kernel regression, and the like. For a more detailed description of machine learning systems and algorithms, see U.S. patent application Ser. No. 10/608,300, titled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety.

Figure 1B:
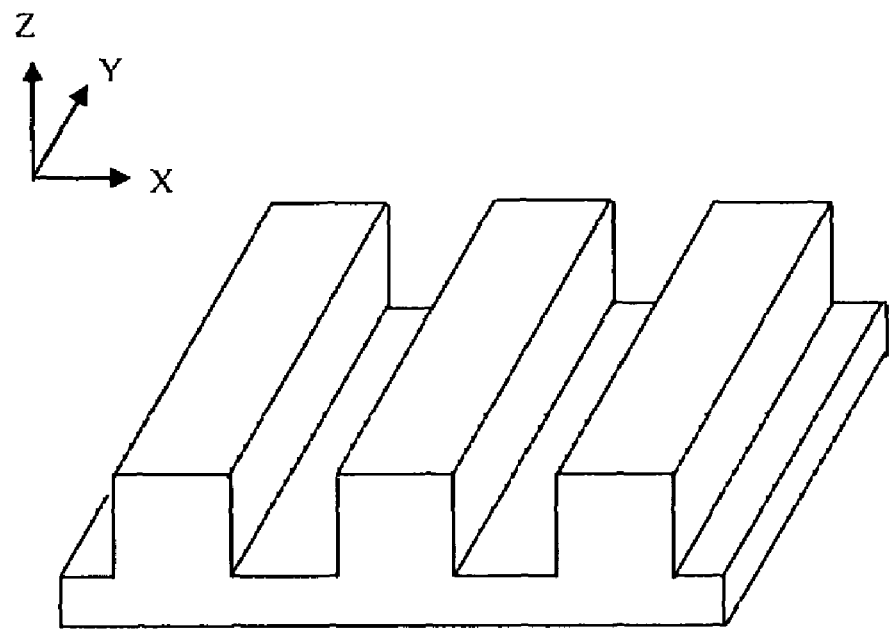
FIG. 1B depicts an exemplary one-dimension repeating structure.

The term "one-dimension structure" is used herein to refer to a structure having a profile that varies in one dimension. For example, FIG. 1B depicts a periodic grating having a profile that varies in one dimension (i.e., the x-direction). The profile of the periodic grating depicted in FIG. 1B varies in the z-direction as a function of the x-direction. However, the profile of the periodic grating depicted in FIG. 1B is assumed to be substantially uniform or continuous in the y-direction.

Figure 1C:
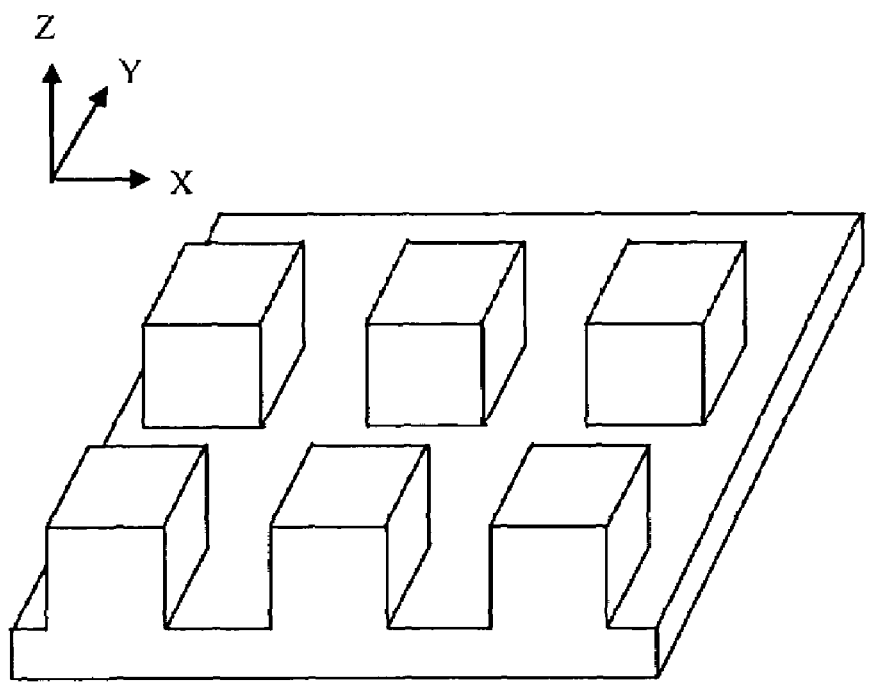
FIG. 1C depicts an exemplary two-dimension repeating structure

The term "two-dimension structure" is used herein to refer to a structure having a profile that varies in two-dimensions. For example, FIG. 1C depicts a periodic grating having a profile that varies in two dimensions (i.e., the x-direction and the y-direction). The profile of the periodic grating depicted in FIG. 1C varies in the z-direction.

Figure 2A:
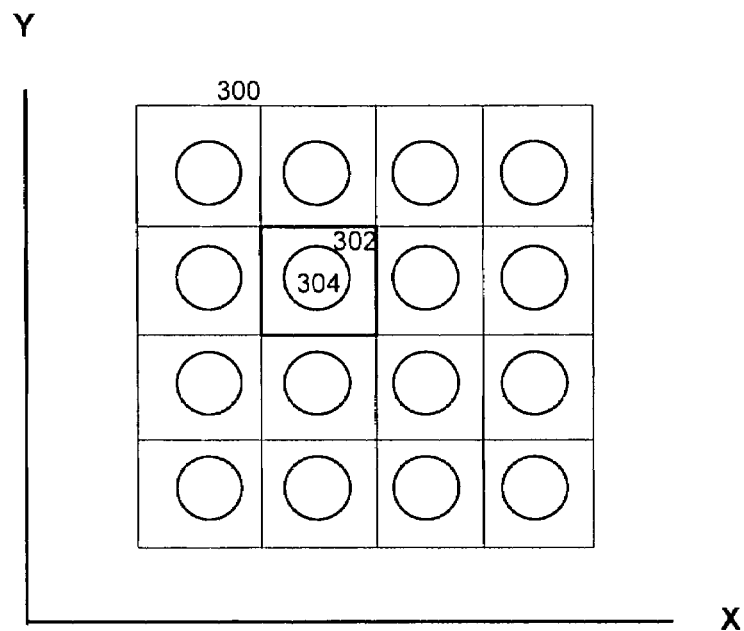
FIG. 2A depicts exemplary orthogonal grid of unit cells of a two-dimension repeating structure.

Discussion for FIGS. 2A, 2B, and 2C below describe the characterization of two-dimension repeating structures for optical metrology modeling. FIG. 2A depicts a top-view of exemplary orthogonal grid of unit cells of a two-dimension repeating structure. A hypothetical grid of lines is superimposed on the top-view of the repeating structure where the lines of the grid are drawn along the direction of periodicity. The hypothetical grid of lines forms areas referred to as unit cells. The unit cells may be arranged in an orthogonal or non-orthogonal configuration. Two-dimension repeating structures may comprise features such as repeating posts, contact holes, vias, islands, or combinations of two or more shapes within a unit cell. Furthermore, the features may have a variety of shapes and may be concave or convex features or a combination of concave and convex features. Referring to FIG. 2A, the repeating structure 300 comprises unit cells with holes arranged in an orthogonal manner. Unit cell 302 includes all the features and components inside the unit cell 302, primarily comprising a hole 304 substantially in the center of the unit cell 302.

Figure 2B:
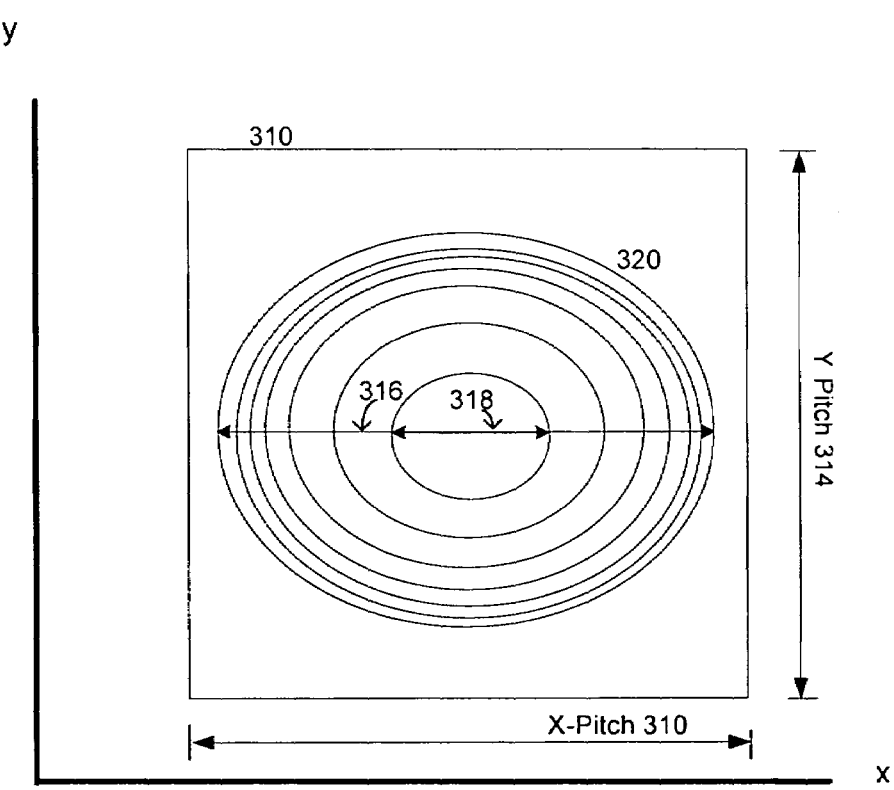
FIG. 2B depicts a top-view of a two-dimension repeating structure.

FIG. 2B depicts a top-view of a two-dimension repeating structure. Unit cell 310 includes a concave elliptical hole. In FIG. 2B, unit cell 310 includes a feature 320 that comprises an elliptical hole, where the dimensions become progressively smaller until the bottom of the hole. Profile parameters used to characterize the structure includes the X-pitch 310 and the Y-pitch 314. In addition, the major axis of the ellipse 316 that represents the top of the feature 320 and the major axis of the ellipse 318 that represents the bottom of the feature 320 may be used to characterize the feature 320. Furthermore, any intermediate major axis between the top and bottom of the feature may also be used as well as any minor axis of the top, intermediate, or bottom ellipse, (not shown).

Figure 2C:
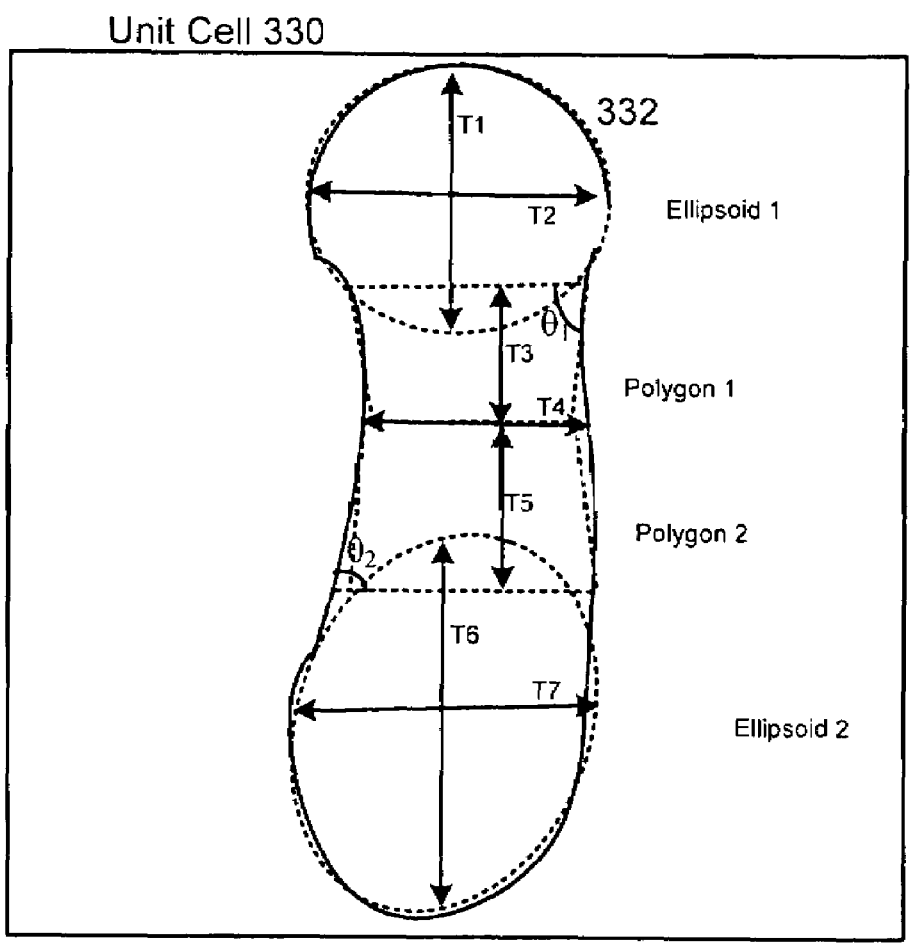
FIG. 2C is an exemplary technique for characterizing the top-view of a two-dimension repeating structure.

FIG. 2C is an exemplary technique for characterizing the top-view of a two-dimension repeating structure. Unit cell 330 includes a feature 332, an island with a peanut-shape viewed from the top. One modeling approach includes approximating the feature 332 with a variable number or combinations of ellipses and polygons. Assume further that after analyzing the variability of the top-view shape of the feature 332, it was determined that two ellipses, Ellipsoid 1 and Ellipsoid 2, and two polygons, Polygon 1 and Polygon 2, were found to fully characterize feature 332. In turn, parameters needed to characterize the two ellipses and two polygons comprise nine parameters as follows: T1 and T2 for Ellipsoid 1; T3, T4, and $\theta_1$ for Polygon 1; T4, T5, and $\theta_2$ for Polygon 2; and T6 and T7 for Ellipsoid 2. Many other combinations of shapes could be used to characterize the top-view of the feature 332 in unit cell 330. For a detailed description of modeling two-dimension repeating structures, refer to U.S. patent application Ser. No. 11/061,303, OPTICAL METROLOGY OPTIMIZATION FOR REPETITIVE STRUCTURES, filed on Apr. 27, 2004, which is incorporated herein by reference in its entirety.

Figure 3:
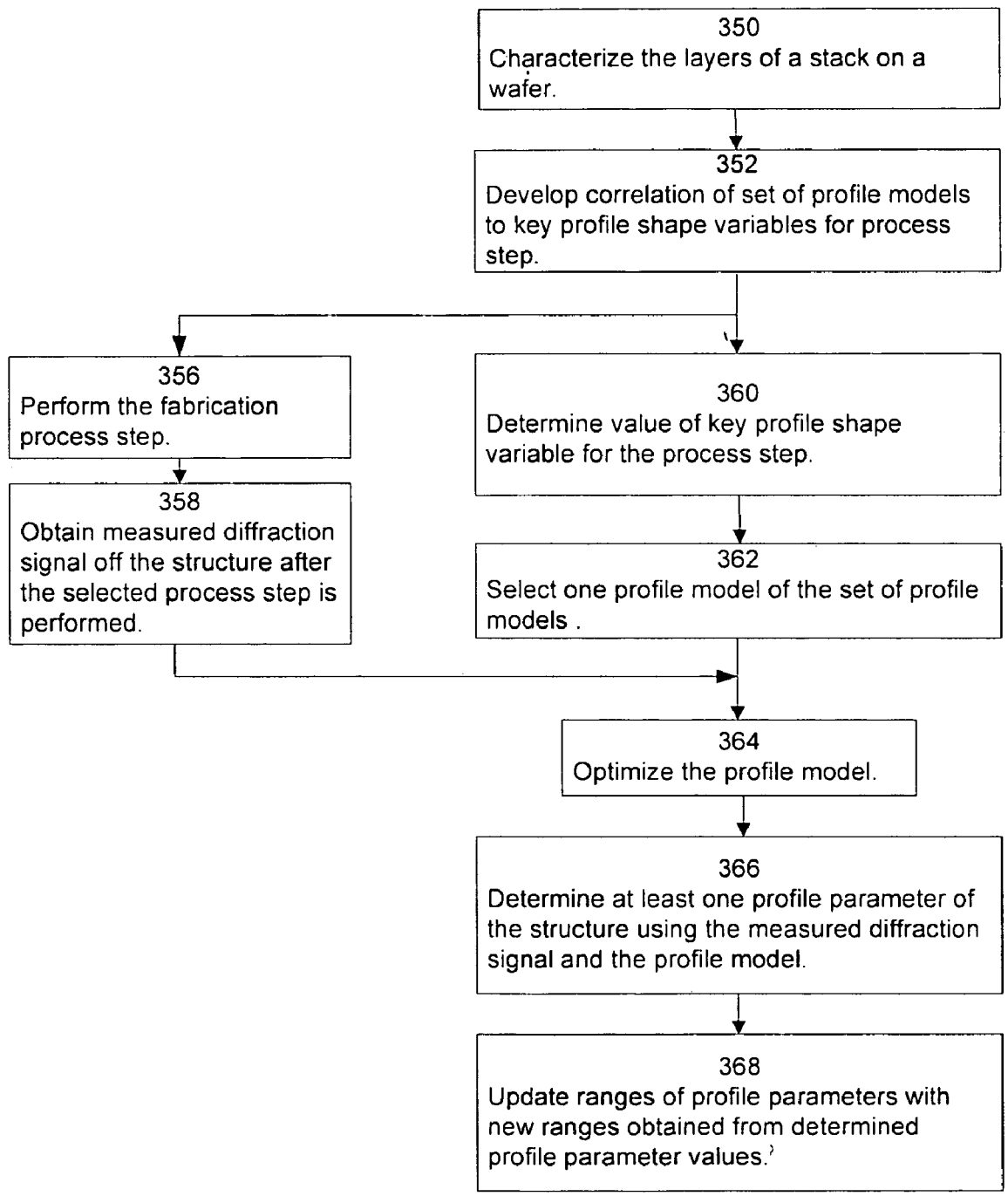
FIG. 3 is an exemplary flowchart for determining one or more profile parameters of a structure.

FIG. 3 is an exemplary flowchart for determining one or more profile parameters of a structure fabricated on a wafer in a wafer application. The wafer application has one or more process steps and one or more process parameters.

In step 350, the layers of a stack on a wafer are characterized. Typically, the layers of the stack of a wafer structure, including any thin film layers under the wafer structure, can be characterized by identifying the type of material, refractive indices, and thickness of each layer. The type of material used in a layer is generally specified in the recipe for the application. The refractive indices, comprising the refractive index n and the extinction coefficient k, are obtained from empirical data or measured using scatterometry devices. Step 350 can be omitted in some applications, such as when the layers of the stack are known in advance.

Figure 4A:
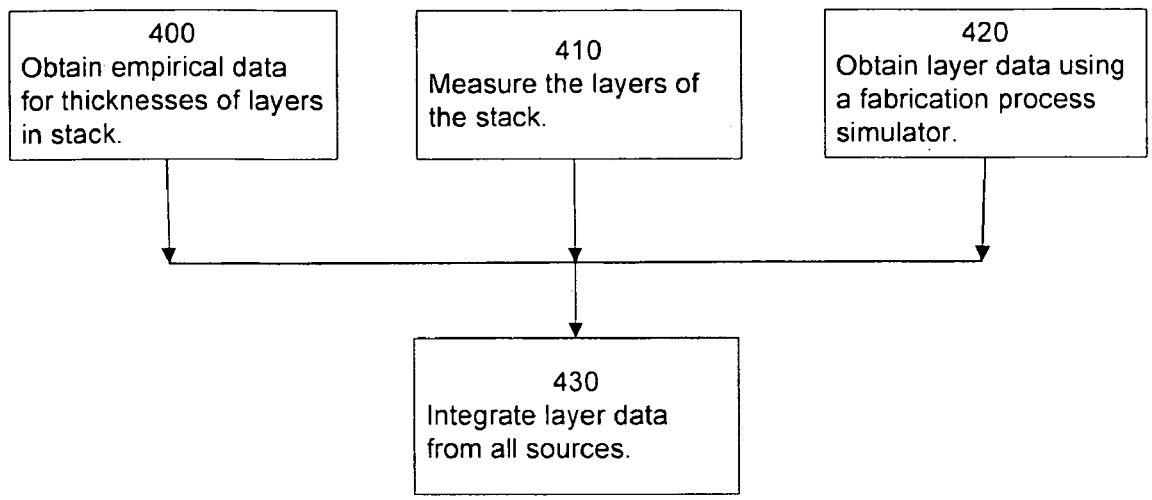
FIG. 4A is an exemplary flowchart of steps for obtaining and integrating layer data of the wafer structure.

FIG. 4A is an exemplary flowchart of steps for obtaining and integrating layer data of the wafer structure. In step 400, empirical data thicknesses of layers in the stack are obtained. The thickness of each layer is typically expressed as a nominal thickness and a low range and high range of the thickness. In step 410, the layers of the stack are measured with scatterometry devices, such as ellipsometers, reflectometers, and the like. Several measurements of the layers are processed using statistical algorithms to determine the nominal thickness and a low range and high range of the thickness. In step 420, the layer data may be obtained using a fabrication process simulator. Examples of process simulators include Athena™ from Silvaco International, Prolith™ from KLA-Tencor, Solid-C from Sigma-C Gmbh, and TCAD™ from Synopsis. In step 430, the various sources of information, including the specifications contained in the recipe for the wafer application, are integrated to provide characterization of the layers of the structure.

Referring to FIG. 3, in step 352, the correlation between a set of profile models and one or more key profile shape variables is developed. Each profile model can be defined using a set of profile parameters to characterize the shape of the structure. For example, the set of profile parameters of a profile model can characterize a rectangular, a trapezoidal, a double trapezoidal, or a triple trapezoidal shape. The shape of the structure can include rounded top, T-top, undercut, or footing features.

Different sets of profile parameters define profile models in the set. For example, one set of profile parameters that defines one profile model can include a bottom width parameter, a top width parameter, and a height parameter. Another set of profile parameters that defines another profile model can include a bottom width parameter, a middle width parameter, a top width parameter, and a height parameter.

The one or more key profile shape variables include one or more profile parameters or one or more process parameters. For example, the one or more key profile shape variables can include only profile parameters (e.g., dimensions of a mask used in the process step, one or more critical dimensions of the structure, height and/or side wall angle of the structure, or a major axis and/or a minor axis of a contact hole), only process parameters (e.g., dose and/or focus for a photolithography process; etchant, etch chamber pressure and/or temperature for an etch process; chamber pressure and/or type of precursor vapor for a chemical vapor deposition, or length of time of a CMP step in a CMP process), or a combination of profile parameters and process parameters.

Figure 4B:
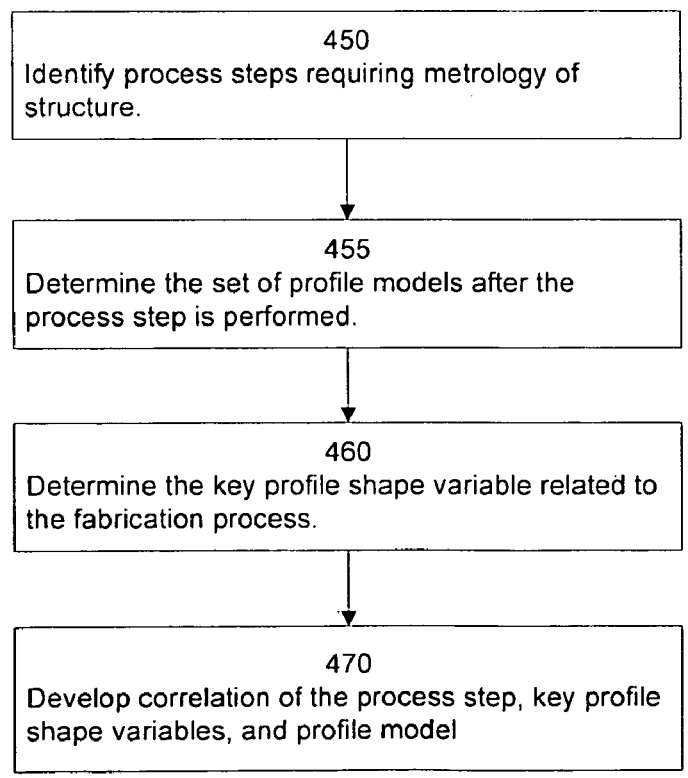
FIG. 4B is an exemplary flowchart for determining and correlating the profile models and key profile shape variables to the process step.

An exemplary method of developing the correlation between a set of profile models and one or more key profile shape variables is depicted in FIG. 4B. Referring to FIG. 4B, in step 450, the fabrication process steps that require metrology of the structure are identified. For example, fabrication process steps that typically add or remove material to a wafer, such as development in photolithography, etching, physical vapor deposition (PVD), chemical vapor deposition (CVD), ion implantation and diffusion, CMP, and photoresist stripping, typically require metrology. Other steps, such as drying and thermal processes, typically do not require metrology.

Figure 5A:
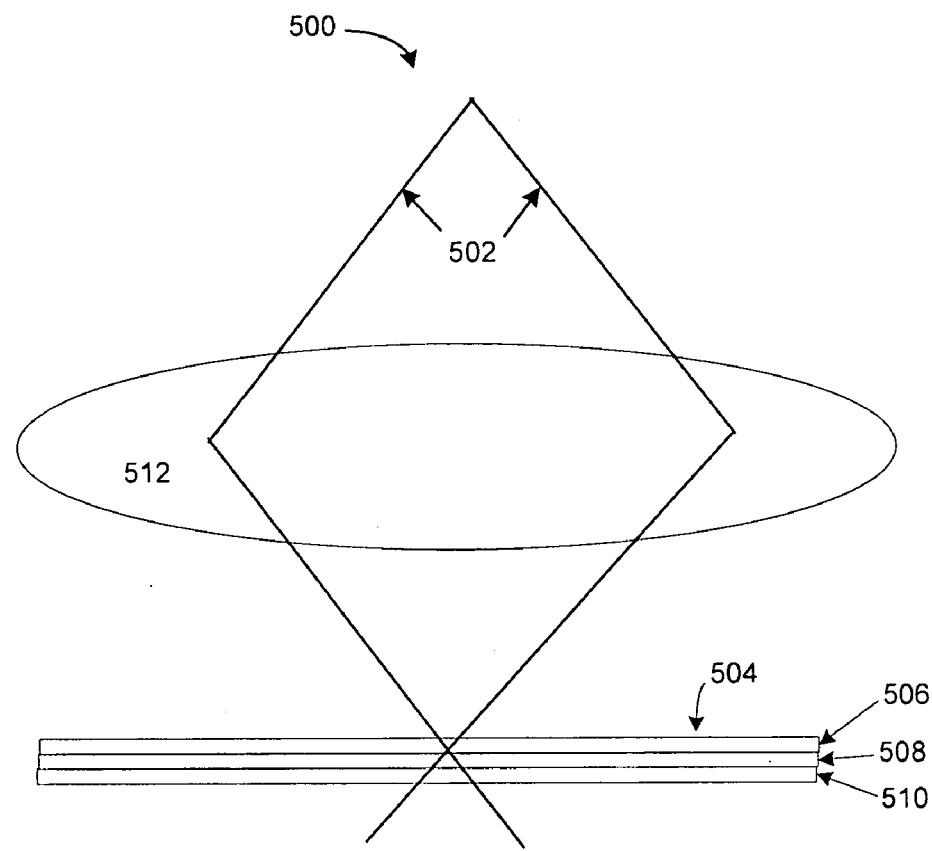
FIG. 5A is an exemplary architectural diagram of a photolithographic apparatus where profile models of the structure is related to values of the process parameters.

In step 455 of FIG. 4B, the set of profile models that characterizes the probable shapes of the structure after the process step is determined. To illustrate this step, FIGS. 5A, 5B, and 5C involving a photolithographic process will be discussed. FIG. 5A is an exemplary architectural diagram of a photolithographic apparatus 500, where the probable shapes of the structure is related to values of the process parameters. A stepper (not shown) projects a beam 502 through a focusing lens 512 onto a site in the wafer 504. The wafer 504 includes a top layer of photoresist 506, a bottom anti-reflective coating (BARC) 508, and the substrate 510. The stepper is set to focus the beam 502 at the photoresist 506 to cause later development of the photoresist 506

Figure 5B:
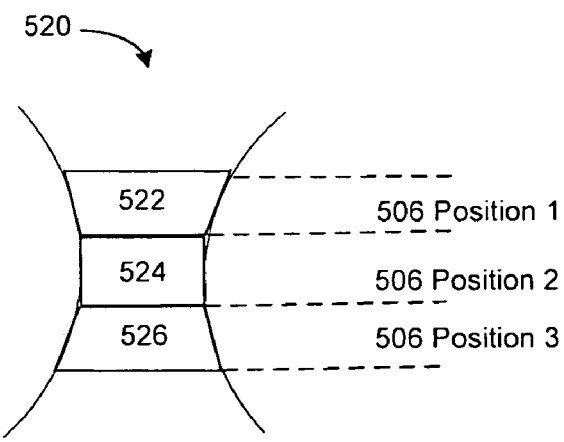
FIG. 5B is an exemplary close-up architectural diagram of the beam used to expose resist in a photolithographic process.

FIG. 5B is an exemplary close-up diagram of the beam profile used to expose resist in a photolithographic process in a shallow trench isolation (STI) application. The beam profile 520 at the point of contact with the photoresist 506 is shown in three positions. If the photoresist 506 is exposed to the beam 502 (FIG. 5A) in Position 1, the profile of the beam 502 (FIG. 5A) approximates an inverted trapezoid shape 522. After development of the exposed photoresist 506, the probable shape of the trench will be similar to the beam profile 522, an inverted trapezoid.

Still referring to FIG. 5B, if the photoresist 506 is exposed to the beam 502 (FIG. 5A) in Position 2, the profile of the beam 502 (FIG. 5A) approximates the rectangular shape 524. After development of the exposed photoresist 506, the probable shape of the trench will be similar to the beam profile 524, a rectangle. If the photoresist 506 is exposed to the beam 502 (FIG. 5A) in Position 3, the profile of the beam 502 (FIG. 5A) approximates a trapezoid shape 526. After development of the exposed photoresist 506, the probable shape of the trench will be similar to the beam profile 526, a trapezoid. The profile of the beam 502 (FIG. 5A), consequently the probable shape of the trench, is correlated to the focus of the beam 502 (FIG. 5A).

Figure 5C:
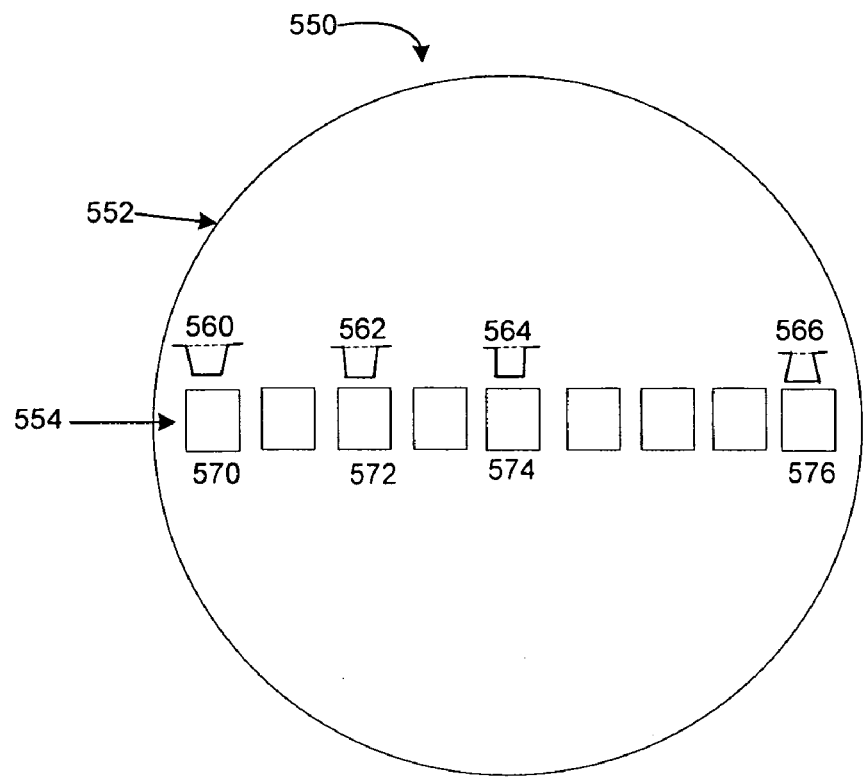
FIG. 5C is an exemplary architectural diagram of a focus exposure monitor wafer.

FIG. 5C is an exemplary architectural diagram of a focus exposure monitor (FEM) wafer 550 highlighting the distribution of probable shapes of the structure as a function of site within the wafer 550. The wafer 550, viewed from the top, includes a series of measurement sites 554 across the diameter of the wafer 550. On the leftmost measurement site 570, the corresponding shape of the trench 560 is shown as an inverted trapezoid. At the third measurement site 572 to the right, the shape of the trench is still an inverted trapezoid 562, but the longer parallel side on top is shorter compared to the longer parallel side in the inverted trapezoid 560. At the middle measurement site 574, the shape of the trench corresponds to rectangular shape 564. At the rightmost measurement site 576, the profile shape of the trench corresponds to a trapezoid 566. The FEM wafer shows that focus and exposure or dose, measured in focus offset typically in microns and milli-joules per $cm^2$, respectively, are key profile shape variables that significantly affect the shape of the structure.

Referring to FIG. 4B, in step 460, the key profile shape variables related to the fabrication process are determined. In step 470, the correlation of the process step, key profile shape variables, and the profile model is developed.

As mentioned above, for a photolithography process, the key profile shape variables can include dose and/or focus. For a photolithography process, the key profile shape variables can also include dimensions of holes in the mask and certain resist parameters, such as inhibitor concentration, diffusion coefficient, Dill parameters, and development rate during the development.

For an etch process, the key profile shape variable can include type of etchants, etch chamber pressure and/or temperature, and the beginning profile parameter values of the profile. For example, if only a top layer of structure is being etched out, then the key profile shape variable can include the profile parameters that characterize the original shape of the structure, where the sidewall angle and a top width of the unetched layer have the greatest affect on the shape of the structure after the etch is done.

For a chemical vapor deposition, the key profile shape variables can include chamber pressure and/or type and flow rate of precursor vapor used. Similarly, for a CMP process, the key profile shape variables can include length of time the CMP process is performed.

For process steps that simply add a layer, such as plating or removing a layer, the effect of process parameters in the ending shape of the structure is minimal. Thus, the key profile shape variables can include the profile parameters that characterize the shape of the structure before the process. For example, if the via in an application is rectangular or inverse trapezoid at the beginning of plating, the shape of the structure will still be a rectangular or inverse trapezoidal shape after the plating. In a CMP, if the shape of the structure underneath the layer at the beginning of polishing is a trapezoid, it generally will be a trapezoid at the end of CMP.

In some complex etch process steps, the key profile variables may be a combination of process parameters and profile parameters. For example, if the beginning shape of a structure is a double or triple trapezoidal shape, the ending shape after the etch may be determined by the etch time and the thicknesses of the trapezoids and sidewall angles.

The key profile shape variables can include profile parameters that characterize the shape of the structure at the beginning of the process step. Values for the key profile shape variables may be the values of the profile parameters at the beginning of the process step. The following example illustrates how the bottom CD and side wall angle affect the profile shape of the structure after the process step is performed.

Figure 6A:
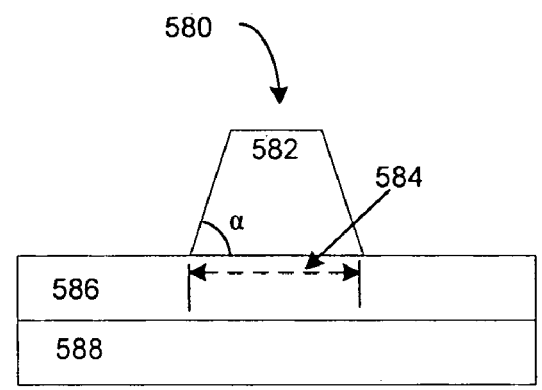
FIGS. 6A and 6B are exemplary architectural diagrams highlighting key profile variables based on starting values of profile parameters.
Figure 6B:
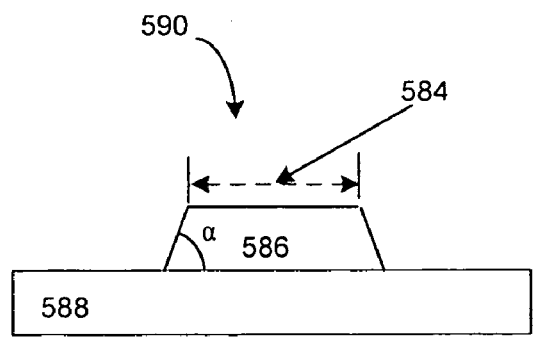

Selection of key profile shape variables from the profile parameters of the structure is illustrated for a metal stack patterning step using mask lithography in FIGS. 6A and 6B. FIGS. 6A and 6B are exemplary architectural diagrams highlighting key profile shape variables that include profile parameters that characterize the shape of wafer structure 580 before metal stack patterning step.

In particular, FIG. 6A illustrates an exemplary diagram of the wafer structure 580 after exposure and development of resist 582 on a metal stack 586 above a glass layer 588 prior to a subsequent etch step. The resist 582 has a sidewall angle α and bottom CD 584 corresponding to the base of the trapezoidal resist structure 582. The value of the sidewall angle α and the value of the bottom CD 584 are noted at the beginning of the etch step. After the etch step, the resulting wafer structure 590 is illustrated in FIG. 6B, where the resist is totally removed and part of the metal stack layer 586 is removed from both sides of the bottom of the resist 582 (FIG. 6A). The structure 586 that remains after the etch step has a trapezoidal profile with the same sidewall angle α as the sidewall angle of the resist 582 (FIG. 6A) that was removed by the etch process. Furthermore, the bottom CD of the resist 582 in FIG. 6A is the same as the top CD of the metal pattern 586. The glass layer 588 remained the same as before the process step. The selected key profile shape variables for the etch step illustrated in FIGS. 6A and 6B are the bottom CD of the resist 582 and the sidewall angle α of the resist 582. For example, if the sidewall angle α is close to ninety degrees, the metal pattern 586 shape after the etch step is likely to be a rectangle. Similarly, if the sidewall angle α is significantly less than ninety degrees, as shown in FIG. 6A, the likely shape is a regular trapezoid. Thus, the bottom CD 584 of the resist 582 determines the top CD of the resulting metal pattern after the etch step.

Figure 7A:
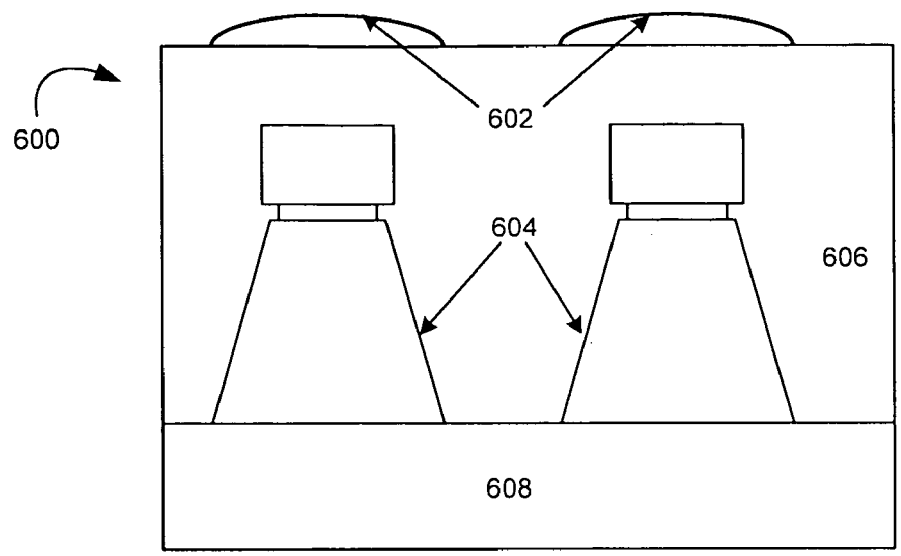
FIGS. 7A, 7B, and 7C are exemplary architectural diagrams highlighting key profile shape variables in a chemical mechanical planarization (CMP) application.
Figure 7B:
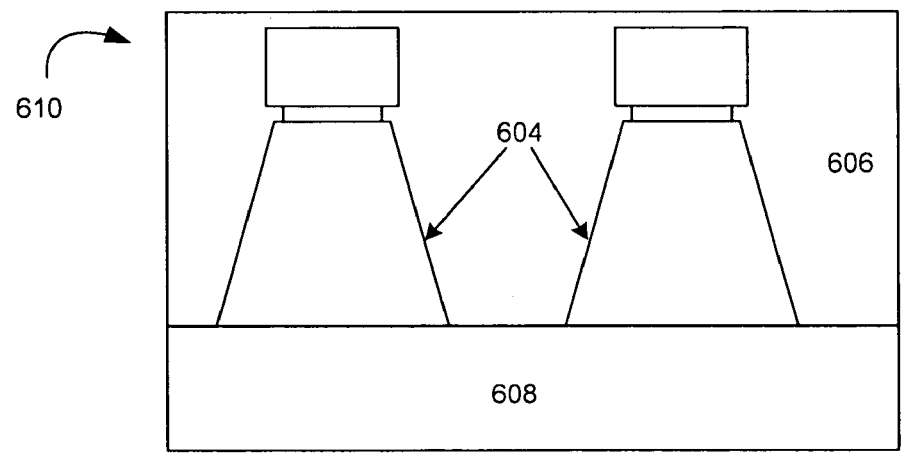
Figure 7C:
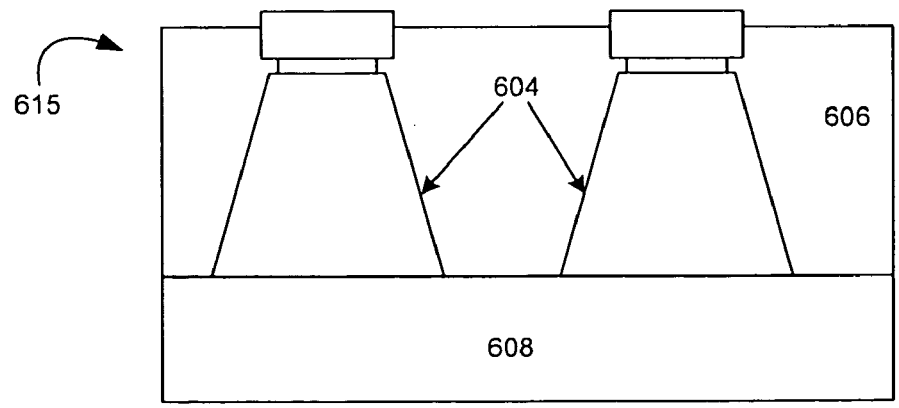

FIGS. 7A, 7B, and 7C are exemplary architectural diagrams highlighting key profile shape variables in a chemical-mechanical-polishing (CMP) application. Referring to FIG. 7A, in a hypothetical fabrication process, a wafer structure 600 includes a repeating structure 604 in a layer after oxide deposition but prior to a first CMP process step. The repeating structure 604 is in a layer above the substrate 608, and has a profile that comprises a trapezoid at the base, a first rectangle smaller than the top thickness of the trapezoid, and a second rectangle that has a slightly larger bottom thickness than the first rectangle. Above the repeating structure are additional oxide 606 and a bump 602 covering an area centered on each feature of the repeating structure 604.

There are several stages of a CMP process that successively remove material from the wafer structure. FIG. 7B illustrates an exemplary diagram of repeating structure 604 where the CMP process removes the bump 602 (FIG. 7A) including some portion of the oxide deposit 606 above the repeating structure 604. Since there was no change in the repeating structure 604 shape, the key profile shape variables are the same as those at the beginning of the CMP process step, namely, the widths and height of the trapezoid and the rectangles. After a subsequent CMP process step as illustrated in FIG. 7C, additional material, such as the oxide deposit 606, is removed without altering the shape of the repeating structure 604. Thus, the key profile shape variables are the same as those at the beginning of the CMP process step. Fabrication process steps that do not alter the shape of the repeating structure typically may use the previous values and ranges of the key profile shape variables for metrology purposes.

Figure 8A:
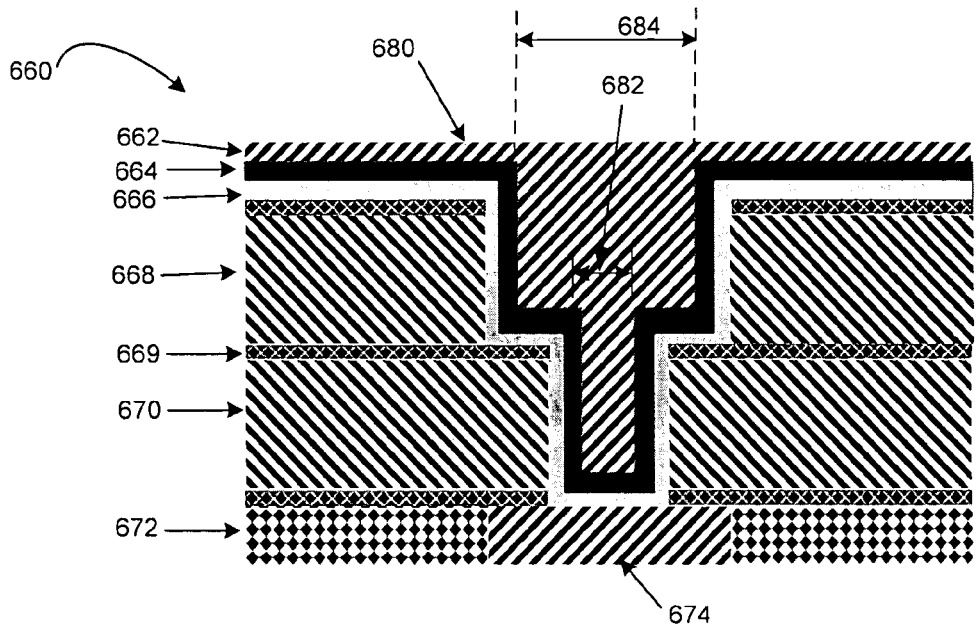
FIGS. 8A and 8B are exemplary architectural diagrams depicting the effect of key profile shape variables in a lithography, etch, and CMP applications.
Figure 8B:
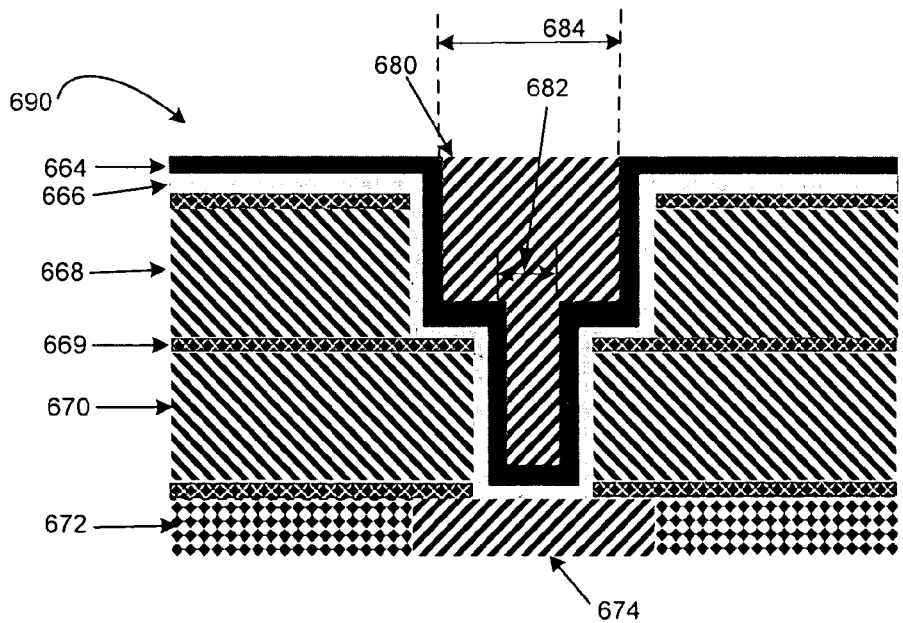

Similarly, certain fabrication process steps that add material to the structure may not alter the basic shape of the repeating structure. FIGS. 8A and 8B are exemplary architectural diagrams depicting key profile shape variables in plating and CMP applications. Referring to FIG. 8A, wafer structure 660 depicts an etched via 680 filled with a barrier layer 666, a seed layer 664, and a copper layer 662. The via was etched on two layers of insulators 668 and 670 separated by an etch stop 669. The substrate 672 was also etched to place a copper interconnect 674. Prior to the beginning of the plating step, the barrier layer 666 was added to the structure and subsequently the seed layer 664 was also added. At the beginning of the plating process step, the key profile shape variable is the top width of the via 684 produced from previous steps. The other key profile shape variable is the width of the via in the lower portion of the via 682. Referring to FIG. 8B, at the end of a CMP process to remove the excess copper plating, the copper deposited above the seed layer 664 is removed. As mentioned above, in a CMP process example, the key profile shape variables are the top width of the via 684 and the inner width of the via 682.

Referring to FIG. 3 in step 360, a value of at least one key profile shape variable of the process step of the wafer application to be used in fabricating the structure is determined. This value may be obtained using a measured value, empirical value, data from the recipe, and/or a result obtained from a previous process step. A measured value for a key profile shape variable that is a process parameter may be obtained from measurement of the process parameter using appropriate sensors. For example, if dose and focus for an exposure step are the key profile shape variables in the development step, then the dose and focus values measured for the exposure step are used. If middle width and sidewall angle are key profile shape variables, then these parameters may be measured with a metrology device, such as a AFM, SEM, and the like. Empirical values, such as those obtained from previous manufacturing runs of the same recipe or similar recipe, may also be used. Key profile shape variables that include profile parameters may also use the nominal values of the profile parameters indicated in the recipe. If values of the profile parameter are typically determined using metrology systems, such as scatterometry, for the previous process step, then those values may be used.

In step 362, one profile model from the set of profile models is selected based on the correlation determined in step 352 and the value of the at least one key profile shape variable determined in step 360. As mentioned above in the photolithography example, the value of the exposure focus determines the shape of the structure. Thus, for a photolithography process, for the value of the exposure focus determined in step 360, the profile model correlated to that value of the exposure focus in the set of profile models is selected. In the CMP or simple etch process, the values of top width and sidewall angle determine the resulting shape of the structure. Thus, for a CMP or simple etch process, for the values of the top width and sidewall angle determined in step 360, the profile model correlated to those values of the top width and sidewall angle in the set of profile models is selected.

In step 356, the fabrication process step is performed using the value of the at least one key profile shape variable determined in step 360 in the fabrication of the structure. For example, for a photolithography process, the value of the exposure focus determined in step 360 can be used to perform the photolithography process to fabricate the structure. For a CMP or simple etch process, the value of top width and sidewall angle determined in step 360 are the values of the corresponding parameters at the beginning of the CMP or simple etch process.

After the structure is fabricated in step 356, in step 358, a measured diffraction signal off the structure is obtained. In one exemplary embodiment, the measured diffraction signal can be measured using optical metrology system 40 depicted in FIG. 1A.

As depicted in FIG. 3, steps 356 and 358 can be performed parallel to steps 360 and 362. Alternatively, steps 356 and 358 can be performed subsequent to steps 360 and 362.

In step 364, the selected profile model can be optimized. For a detailed description of optimizing a profile model for a two-dimension repeating structure, refer to U.S. patent application Ser. No. 11/061,303, OPTICAL METROLOGY OPTIMIZATION FOR REPETITIVE STRUCTURES, by Vuong, et al., filed on Apr. 27, 2004, and is incorporated in its entirety herein by reference. It should be recognized, however, that step 364 can be omitted in some applications.

In step 366, at least on profile parameter of the structure is determined using the measured diffraction signal and the selected profile model, whether optimized or not. In another embodiment, all the profile parameters of the structure are determined, including the CD and underlying thickness of the stack. As described above, the one or more profile parameters of the structure can be determined by comparing the measured diffraction signal to simulated diffraction signals generated using the selected profile model. In step 368, ranges of the profile parameters are updated based on the values of the profile parameters determined in step 366.

Figure 9:
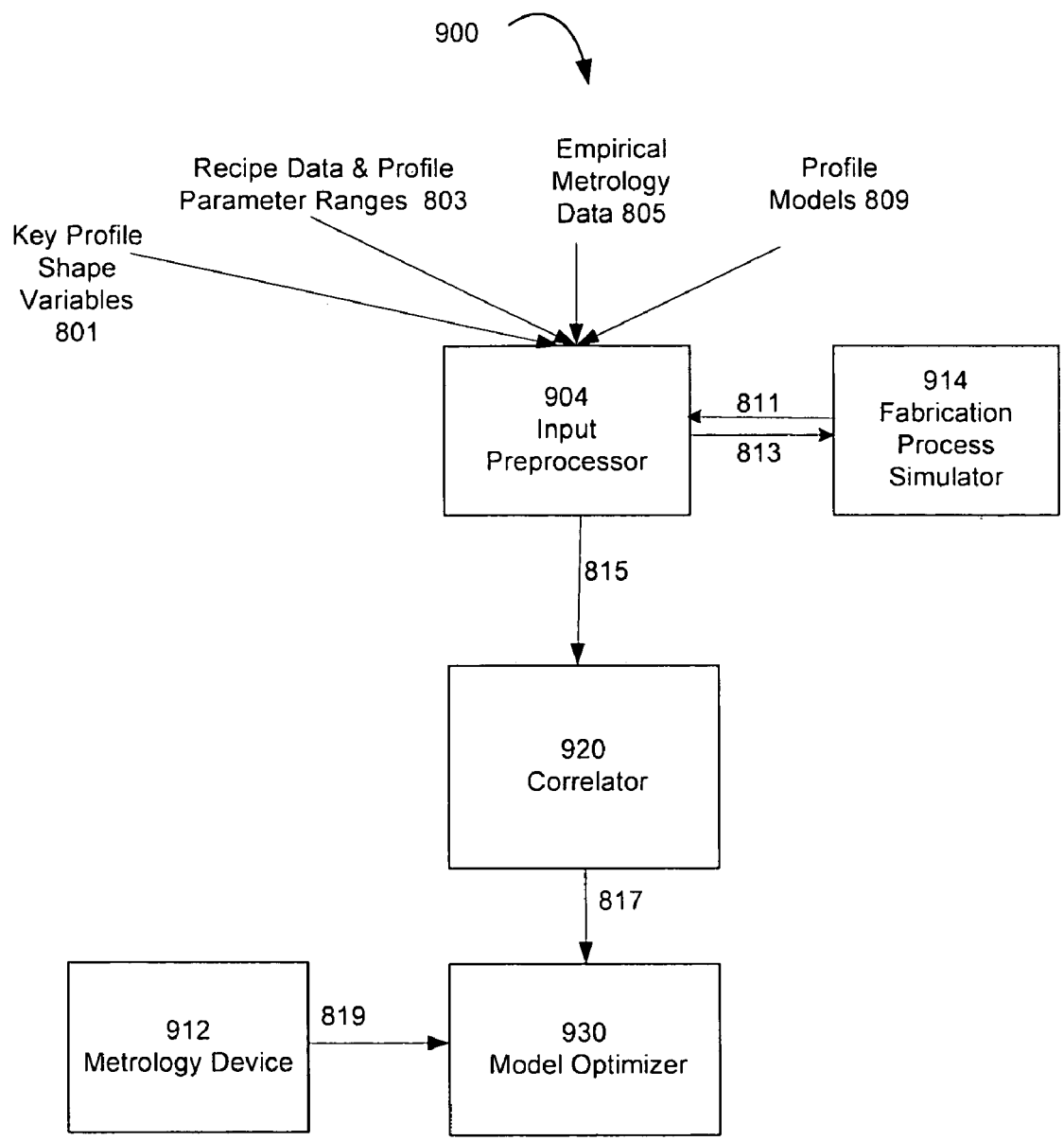
FIG. 9 is an exemplary architectural diagram of a system configured to develop a correlation of profile models of the structure and key profile shape variables.

FIG. 9 is an exemplary architectural diagram of a system 900 configured to develop a correlation of process step, profile models of the structure, and key profile shape variables. The system 900 includes an input preprocessor 904, a fabrication process simulator 914, a correlator 920, a metrology device 912, and a model optimizer 930. The input preprocessor 904 processes input comprising key profile shape variables 801, recipe data and structure profile parameter ranges 803 for each fabrication step that requires metrology, empirical metrology data 805, and profile models 809 for each fabrication step requiring metrology.

Recipe data include identification of the wafer structure application, namely, shallow trench isolation (STI), hard mask open, gate with spacers, deep trench, contact hole, post, and other three dimension repeating structures, such as islands, peanut shape ellipses, and the like. Furthermore, recipe data may also include identification of a set of steps, such as mask lithography, metal stack patterning, photo resist spin on, STI lithography, STI etch, oxide deposition, and different CMP stages. Profile parameter ranges typically include the nominal, high, and low value of profile parameter, such as underlying film thicknesses in the stack, bottom CD, sidewall angle, top CD, and the like. Empirical metrology data includes refraction indices, such as refractive index or extinction coefficients. Profile models can include rectangular, regular trapezoid, inverted trapezoid, double trapezoid, triple trapezoids, or a combination of two or more shapes. A profile model may characterize shape features, such as top rounding, T-topping, footing, or undercut. As mentioned above, two-dimension structures, such as posts, holes, or islands and a post, hole, or island, may be characterized using metrology models with round, square, or elliptical shapes. From a cross-section viewpoint, the two-dimension structure may be concave or convex or a combination of two or more shapes.

Still referring to FIG. 9, fabrication process simulator 914 may be used to simulate a process step and provide parameter ranges, profile models, and refractive indices 811. The input preprocessor 904 may provide ranges of process parameters specified in the recipe, such as dose and exposure 813 for process step, to the fabrication process simulator 914. The process simulator 914 uses the data to generate and transmit the profile model and parameter ranges 811 after completion of the process step simulation. As mentioned above, software, such as Athena™ from Silvaco International, Prolith™ from KLA-Tencor, Solid-C from Sigma-C Gmbh, TCAD™, and the like, may be used to simulate a process step.

Data 815 from the input preprocessor 904 are transmitted to the correlator 920, where the profile models and key profile shape variables are correlated for the process steps requiring metrology. An example of a correlation may include the development step of photolithography process, where the key profile shape variables include focus and dose of the stepper used in exposing the mask and the mask opening dimension. As another example of a correlation, for a given dose and mask opening dimension, assume that a low value of the focus results in an inverted trapezoid, while a high value of the focus results in a regular trapezoid, and a median value of the focus results in a rectangular shape. As another example, for a given dose and focus of the exposure step, assume that the site on the wafer affects the shape of the structure, starting with an inverted trapezoid at a site at one end of the wafer to a rectangular shape at a site in the middle of the wafer, and a regular trapezoid shape at a site at the opposite end of the wafer.

For each process step requiring metrology, the correlator 920 correlates profile models and key profile shape variables, which may include one or more process parameters, one or more profile parameters, or a combination of one or more process parameters and profile parameters. For lithography and complex etch processes, process variables determine the shape of the structure. For the majority of process steps that basically adds some material or remove material to a structure, the key profile shape variables are profile parameters of the structure shape prior to the process step. A via or contact hole when filled with material does not change shape. Plating with copper or other metal does not change the shape in most cases. CMP and cleaning removes material, but, in the majority of cases, the shape of the structure remains the same. Thus, the key profile shape variables are the profile parameters that characterize the shape of the structure at the beginning of the process.

Correlation may be performed by using ranges of the key profile shape variable values resulting in a profile model. For example, low, medium, and high focus range in the exposure step may correspond to an inverted trapezoid, a rectangular, or a regular trapezoid shape. Similarly, sidewall angle ranges may correspond to specific shapes. Other correlation using linear equations or more complex function may be used to get the shape of two dimension structures. The results of the correlation may be stored in a computer memory or storage device in a table or data base.

Metrology device 912 is used to measure the wafer structure after the process step is completed. The measured diffraction signal 819 is transmitted to the model optimizer 930. Using the correlation generated in the correlator 920, the model optimizer 930 selects the profile model for the step using the values of the key profile shape variables obtained. In some applications, the model optimizer 930 optimizes the selected profile model. The values of the profile shape variables may be obtained using a metrology device, such as an AFM, SEM, reflectometers, ellipsometers, hybrid devices, and the like. Alternatively, as mentioned above, the values of the profile shape variables may be obtained from empirical data or from simulation of the previous step in a process optimizer. The model optimizer 930 generates an optimized profile model of the structure. As noted above, however, in some applications, optimization of the profile model can be omitted.

Using the profile model, measured diffraction signals off the structure measured using the metrology device 912 are used to determine one or more profile parameters of the structure. As described above, a library-based or regression-based process can be used to determine the one or more profile parameters based on the profile model and the measured diffraction signals.

Figure 10:
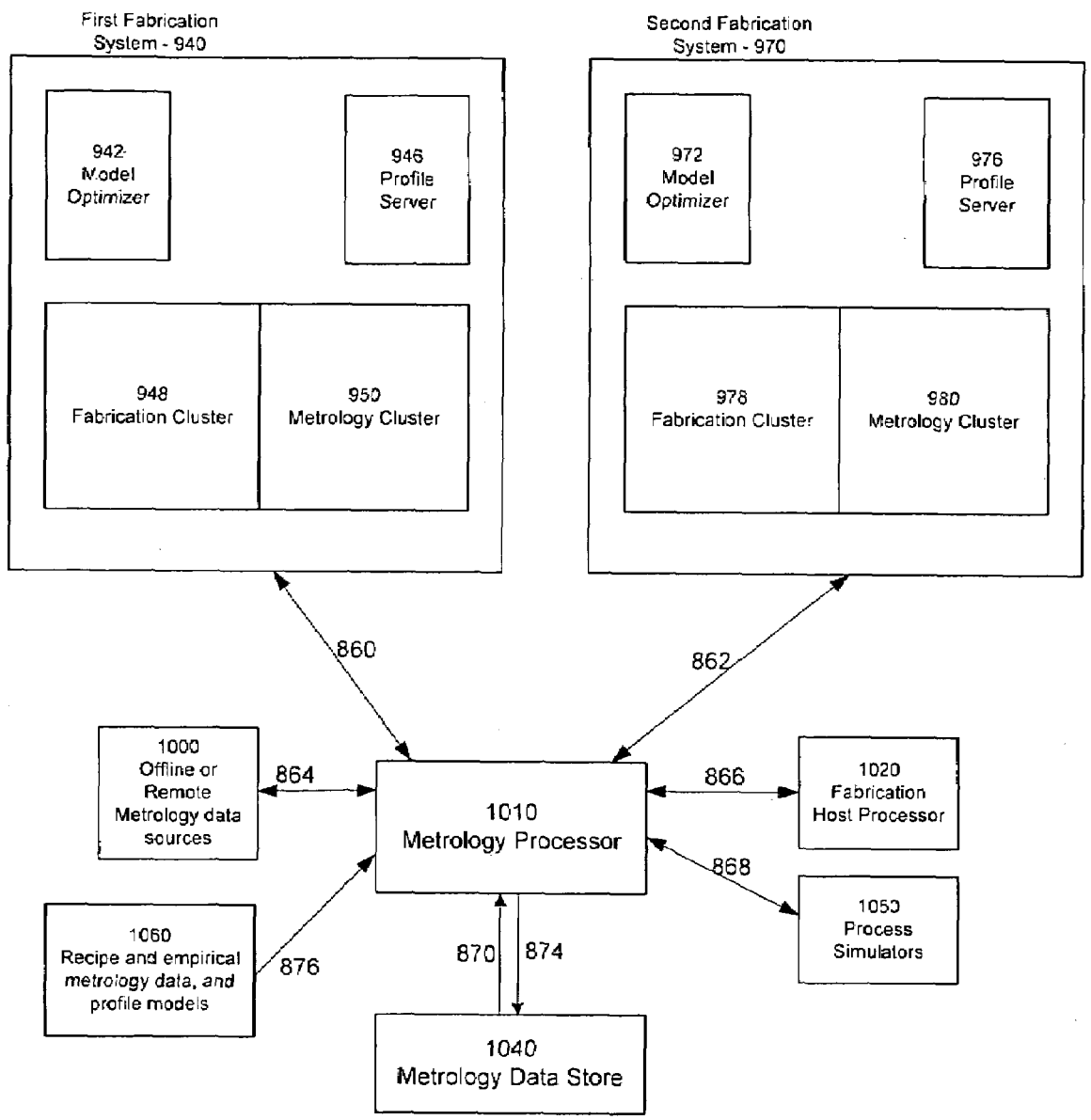
FIG. 10 is an exemplary architectural diagram for linking two or more fabrication systems with a metrology processor and a metrology data store to determine profile parameters of structures.

FIG. 10 is an exemplary architectural diagram for fabrication cluster systems linked with a metrology processor for determining features of wafer structures and using the profile parameters and features of the profile parameters for advanced process control. A first fabrication system 940 includes a model optimizer 942, profile server 946, a fabrication cluster 948, and a metrology cluster 950. The first fabrication system 940 is coupled to a metrology processor 1010. The metrology processor 1010 is coupled to metrology data sources 1000, a metrology data store 1040, and the fabrication host processors 1020. The model optimizer 942 contains the logic to select a profile model of a measurement structure. The model optimizer 942 can also contain the logic to optimize the profile model. The profile server 946 contains the logic to determine one or more profile parameters of the measurement structure based on the measured diffraction signal and the selected profile model. The fabrication cluster 948 may be a track, etcher, deposition process tool. The metrology cluster 950 comprises a set of metrology tools, such an angle-resolved spectroscopic scatterometer. The second fabrication system 970 includes a model optimizer 972, profile server 976, a fabrication cluster 978, and a metrology cluster 980. These devices have the same functions as the equivalent devices in the first fabrication system 940. The first and second fabrication systems 940 and 970 are coupled to metrology processor 1010.

Referring to FIG. 10, the metrology processor 1010 receives metrology data 864 from the offline or remote metrology data sources 1000. The offline metrology data sources 1000 may be an offline cluster of metrology devices in the fabrication site, such as reflectometers, ellipsometers, SEMs, and the like. The remote metrology data sources 1000 may include a remote data server or remote processor or website that provides metrology data for the application. Data 860 from the first fabrication system 940 to the metrology processor 1010 may include the profile parameter ranges of the profile model and the generated data stores to determine the structure features. The metrology data stores 1040 may include a library of pairs of simulated diffraction signals and corresponding sets of profile parameters or a trained MLS system that can generate a set of profile parameters for an input measured diffraction signal. Data 870 from metrology data stores 1040 to metrology processor 1010 includes a set of profile parameters and/or simulated diffraction signal. Data 874 from the metrology processor 1010 to metrology data store 1040 includes values of the profile parameters, material refraction parameters, and metrology device parameters in order to specify the portion of the data space to be searched in the library or trained MLS store in the metrology data store 1040. Data 862 transmitted to and from the second fabrication system 970 to the metrology processor 1010 are similar to the data 860 transmitted to and from the first fabrication system 940.

Still referring to FIG. 10, data 866 transmitted to and from the metrology processor 1010 to the fabrication host processor 1020 may include data related to the application recipe and process data measured by the metrology clusters 950 and 980 in the first and second fabrication systems 940 and 970, respectively. The metrology data store 1040 in FIG. 10 is the repository of metrology data. The metrology data is made available to the first and/or the second fabrication system 940 and 970. As mentioned above, the first and/or second fabrication system 940 and 970 may include one or more of a photolithography, etch, thermal processing system, metallization, implant, chemical vapor deposition, chemical mechanical polishing, or other fabrication unit.

Data on the features of the measurement structures determined by the profile server 946 in the first fabrication system 940 may be transmitted to the fabrication host processor 1020. The data can be used by the fabrication host processor to adjust a process parameter in the fabrication cluster 948 of the first fabrication system 940 or adjust a process parameter in the fabrication cluster 978 of the second fabrication system 970. For example, if the fabrication cluster 948 is a photolithography unit and the fabrication cluster 978 is an etch unit, the data may be top critical dimension of a measurement structure measured by the metrology cluster 950. The value of the top critical dimension may be used by the fabrication host processor 1020 to adjust the focus or exposure of the photolithography unit. Furthermore, the value of the top critical dimension may be used by the fabrication host processor 1020 to adjust an etch variable, such as flow rate of the etchant. In a similar manner, the value of a profile parameter of a measurement structure measured by the metrology cluster 980 and determined by the profile server 976 of the second fabrication system 970 may be transmitted to the fabrication host processor 1020. The value of the profile parameter can be used by the fabrication host processor to adjust a process parameter in the fabrication cluster 948 of the first fabrication system 940 or adjust a process parameter in the fabrication cluster 978 of the second fabrication system 970. It is understood that the second fabrication system may include any fabrication cluster involved in the wafer manufacturing process.

Still referring to FIG. 10, for process steps requiring metrology, the metrology processor 1010 is additionally configured to generate the correlation between a set of profile models and key profile shape variables as depicted in FIGS. 3, 4A, and 4B. Recipe data, profile parameter ranges, empirical metrology data obtained from measurements, and profile models 876 of the wafer structure after a process step is completed are obtained from other computerized sources or manually entered at input 1060. The generated correlation is stored in memory in the metrology processor 1010 or in the metrology data store 1040. The stored correlation is accessed by the model optimizer 942 or 972 via requests to the metrology processor 1010 through links 860 or 862 from the first fabrication system 940 or second fabrication system 970. Profile models for a process step may also be obtained by the metrology processor through link 868 from the process simulators 1050. In alternate embodiments, generation of the correlation may be resident in or performed in any local or remote processor in a facility as long as the access to recipe data, profile parameter ranges, empirical metrology data obtained from measurements, and profile models for the process step. As mentioned above, the configuration of the metrology processor is one exemplar, and many other configurations of where the model optimizers 942 and 972 and profile servers 946 and 976, may be resident in a separate remote or local processor (not shown) or configured to run with the metrology processor 1010.

Figure 11:
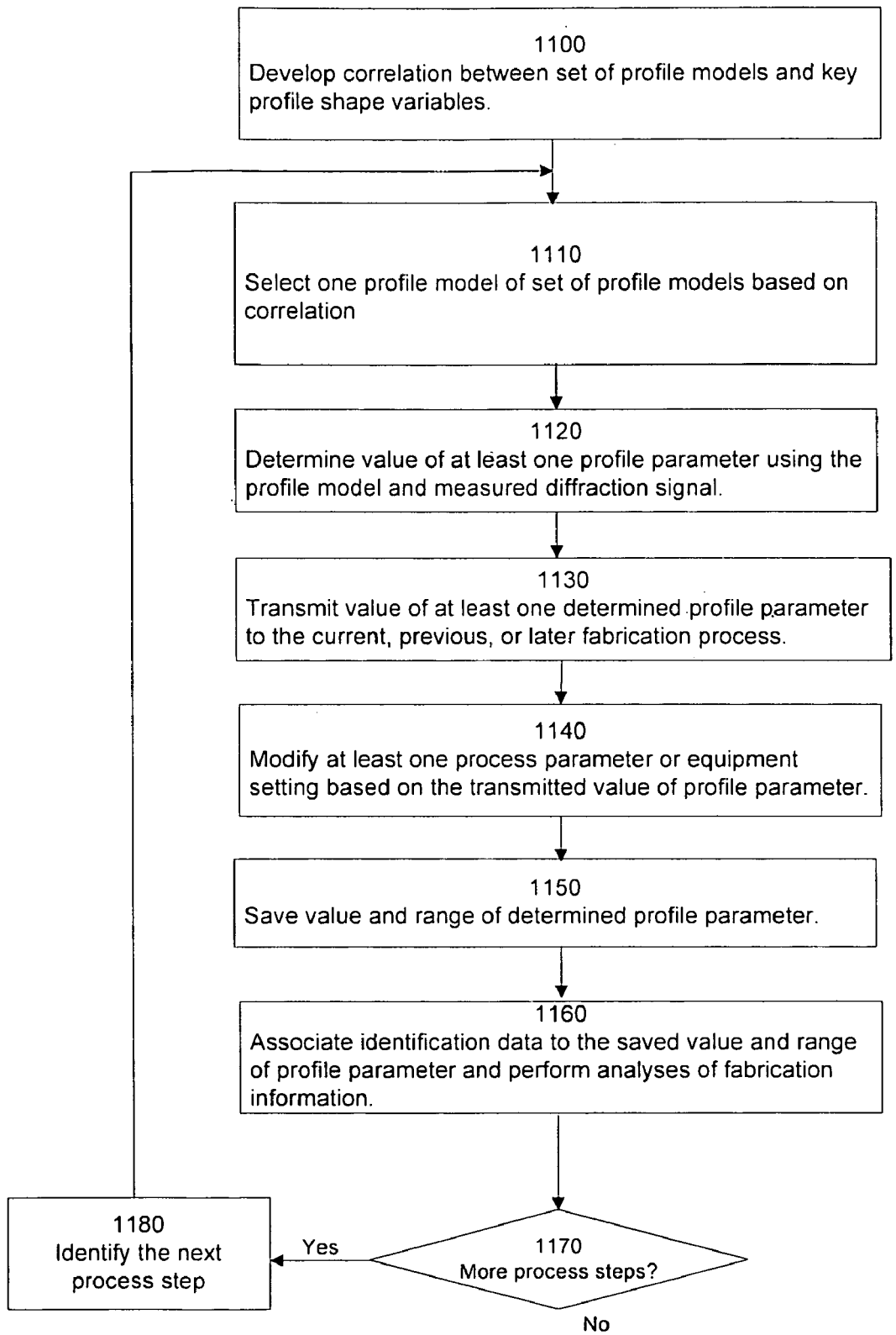
FIG. 11 is an exemplary flowchart for managing and utilizing metrology data for automated process and equipment control.

FIG. 11 is an exemplary flowchart for managing and utilizing metrology data for automated process and equipment control. In step 1100, a correlation between a set of profile models of the wafer structure and key profile shape variables is developed. In step 1110, one profile model from the set of profile models is selected based on the correlation. In step 1120, the value of at least one profile parameter is determined using the profile model and the measured diffraction signal.

In step 1130, the value of the at least one profile parameter is transmitted to the current, previous, or later fabrication process. For example, if the current process step is a development step of a photolithography process, a structure thickness or CD may be transmitted to the developer, to the stepper that performed the exposure, or to an etcher that will perform the etch operation.

In step 1140, at least one process parameter or equipment setting is modified based on the transmitted profile parameter value. Continuing with the example above, a CD of the structure after development of the resist may be sent to the developer and the developer controller may adjust a process parameter based on the value of the CD. Similarly, if the CD is sent to the stepper, the stepper may adjust at least one of the focus or dose or both based on the value of the CD. If the CD is sent to the etcher, the etcher may adjust an etch process parameter, such as pressure or temperature of the etch chamber or time used for etching.

In step 1150, the value and range determined for the profile parameter are saved. This data can be saved in computer storage, such as a database or in computer memory. Furthermore, in step 1160, identification data, such as the application recipe, lot number, wafer number, and site number within the wafer, can be associated to the saved value and range. The fabrication information may be processed with statistical techniques to identify trends and averages.

If there are more process steps, step 11170, the next process step of the application is identified in step 1180. The processing is iterated starting with step 1110.

Although exemplary embodiments have been described, various modifications can be made without departing from the spirit and/or scope of the present invention. Therefore, the present invention should not be construed as being limited to the specific forms shown in the drawings and described above.

We claim:

1. A method of determining one or more profile parameters of a structure fabricated on a wafer in a wafer application, the wafer application having one or more process steps, each process step having a set of process parameters, the method comprising:
    a) for a selected process step of the wafer application, developing a correlation between a set of profile models and at least two key profile shape variables, wherein each profile model is defined using a set of profile parameters to characterize the shape of the structure, wherein different sets of profile parameters define the profile models in the set, and wherein the at least two key profile shape variables are selected from the set of profile parameters and from the set of process parameters having the most effect on the profile shape after the process step of the wafer application is performed, the selection based on sampling of profile shape changes resulting from changes of two process parameters, changes of two profile parameters, or a change of one or more process parameters and/or a change of one or more profile parameters, wherein the correlation between a set of profile models and at least two key profile shape variables is performed using ranges of the set of profile parameters of the structure;
    b) determining a value of at least two key profile shape variables of the process step of the wafer application to be used in fabricating the structure;
    c) selecting one profile model from the set of profile models based on the correlation determined in a) and the value of the at least two key profile shape variable determined in b);
    d) fabricating the structure using the process step and the value of the at least one key profile shape variable determined in b);
    e) obtaining a measured diffraction signal off the structure fabricated in d); and
    f) determining one or more profile parameters of the structure fabricated in d) based on the measured diffraction signal obtained in e) and the profile model selected in c).

2. The method of claim 1, wherein the at least two key profile shape variables in a) include at least two profile parameters.

3. The method of claim 2, wherein the at least two key profile shape variable in b) includes two or more dimensions of a mask used in the process step, two or more critical dimensions of the structure, height and/or side wall angle of the structure, or a major axis and/or a minor axis of a contact hole.

4. The method of claim 1, wherein the at least two key profile shape variables in a) include two or more process parameters.

5. The method of claim 4, wherein:
    if the process step is a photolithography process, the at least two key profile shape variables in b) includes dose and/or focus;
    if the process step is an etch process, the at least two key profile shape variables in b) includes type of etchant, etch chamber pressure, and/or temperature;
    if the process step is a chemical vapor deposition, the at least two key profile shape variables in b) includes chamber pressure and/or type of precursor vapor used; or
    if the process step is a chemical mechanical planarization step, the at least two key profile shape variables in b) includes length of time of the chemical mechanical planarization step is performed.

6. The method of claim 1, wherein the at least two key profile shape variables in a) include a combination of one or more profile parameters and two or more process parameters.

7. The method of claim 1, wherein the process step comprises photo-lithography, metal stack patterning, photo resist spin on, etch, deposition, or chemical mechanical planarization.

8. The method of claim 1, wherein the wafer application comprises a shallow trench isolation, hard mask open, gate with spacers, deep trench, three-dimension structure such as islands and variable shape ellipses; contact hole, or post application.

9. The method of claim 1, wherein the set of profile parameters of the profile model characterizes a rectangular, a trapezoidal, a double trapezoidal, or a triple trapezoidal shape, and wherein the profile model includes rounded top, T-top, undercut, or footing features.

10. The method of claim 1, wherein the set of profile parameters of the profile model characterizes a post, a via, a contact hole, an island, or a cylinder.

11. The method of claim 1, wherein the set of profile parameters of the profile model characterizes a two-dimension shape included within a unit cell.

12. The method of claim 1, further comprising:
characterizing layers of a stack on the wafer.

13. The method of claim 12, wherein characterizing layers of the stack on the wafer comprises:
obtaining a range of thickness for each layer of the stack, the range including a low value, a nominal value, and a high value.

14. The method of claim 13, wherein obtaining the range of thickness of each layer of the stack includes:
using empirical data obtained from previous runs of a similar wafer application;
using data obtained by measuring the layers of the stack; or
using data obtained from simulation of one or more process steps of the wafer application.

15. The method of claim 1 further comprising:
linking the process step to values of the key profile shape variables and the corresponding profile model from the set of profile models.

16. The method of claim 15 further comprising:
storing the process step, the values of the key profile shape variables, and the corresponding profile model from the set of profile models.

17. The method of claim 16 further comprising:
associating fabrication recipe information of the wafer application to the stored process step, the values of the key profile shape variables, and the corresponding profile model from the set of profile models.

18. A method of determining one or more profile parameters of a structure fabricated on a wafer in a wafer application, the wafer application having one or more process steps and one or more process parameters, the method comprising:
a) determining a value of at least one key profile shape variable of a process step of the wafer application to be used in fabricating the structure;
b) selecting one profile model from the set of profile models based on the value of the at least two key profile shape variable determined in a) and a correlation between the set of profile models and at least two key profile shape variables, wherein each profile model is defined using a set of profile parameters to characterize the shape of the structure, wherein different sets of profile parameters define the profile models in the set, and wherein the at least two key profile shape variables are selected from the set of profile parameters and from the set of process parameters having the most effect on the profile shape after the process step of the wafer application is performed, the selection based on sampling of profile shape changes resulting from changes of two process parameters, changes of two profile parameters, or a change of one or more process parameters and/or a change of one or more profile parameters, wherein the correlation between a set of profile models and at least two key profile shape variables is performed using ranges of the set of profile parameters of the structure;
c) obtaining a measured diffraction signal off the structure fabricated using the process step and the value of the at least two key profile shape variable determined in a); and
d) determining one or more profile parameters of the structure based on the measured diffraction signal obtained in c) and the profile model selected in b).

19. The method of claim 18 further comprising:
saving the selected profile model, the associated process step, and the determined value of the at least two key profile shape variables.

20. The method of claim 18 further comprising:
characterizing layers of a stack on the wafer.

21. The method of claim 20, wherein characterizing layers of the stack on the wafer comprises:
obtaining a range of thickness for each layer of the stack, the range including a low value, a nominal value, and a high value.

22. The method of claim 18 further comprising:
linking the process step to values of the key profile shape variables and the corresponding profile model from the set of profile models.

23. A computer-readable storage medium containing computer-executable instructions to determining one or more profile parameters of a structure fabricated on a wafer in a wafer application, the wafer application having one or more process steps and one or more process parameters, the method comprising:
a) determining a value of at least one key profile shape variable of a process step of the wafer application to be used in fabricating the structure;
b) selecting one profile model from the set of profile models based on the value of the at least two key profile shape variable determined in a) and a correlation between the set of profile models and at least two key profile shape variables, wherein each profile model is defined using a set of profile parameters to characterize the shape of the structure, wherein different sets of profile parameters define the profile models in the set, and wherein the at least two key profile shape variables are selected from the set of profile parameters and from the set of process parameters having the most effect on the profile shape after the process step of the wafer application is performed, the selection based on sampling of profile shape changes resulting from changes of two process parameters, changes of two profile parameters, or a change of one or more process parameters and/or a change of one or more profile parameters, wherein the correlation between a set of profile models and at least two key profile shape variables is performed using ranges of the set of profile parameters of the structure;
c) obtaining a measured diffraction signal off the structure fabricated using the process step and the value of the at least two key profile shape variable determined in a); and
d) determining one or more profile parameters of the structure based on the measured diffraction signal obtained in c) and the profile model selected in b).

* * * * *